United States Patent [19]

Bünger et al.

[11] Patent Number: 4,464,477

[45] Date of Patent: Aug. 7, 1984

[54] PROCESS FOR THE RECOVERY AND REUSE OF HEAVY METAL OXIDATION CATALYST FROM RESIDUES IN THE WITTEN DMT PROCESS

[75] Inventors: Heinrich Bünger, Siegburg; Rudolf Cordes; Gerhard Hoffmann, both of Niederkassel, all of Fed. Rep. of Germany

[73] Assignee: Dynamit Nobel Aktiengesellschaft, Troisdorf, Fed. Rep. of Germany

[21] Appl. No.: 326,175

[22] Filed: Dec. 1, 1981

Related U.S. Application Data

[63] Continuation-in-part of Ser. No. 326,280, Dec. 1, 1981, Pat. No. 3,372,875, which is a continuation of Ser. No. 156,605, Jun. 5, 1980, abandoned.

[30] Foreign Application Priority Data

Dec. 2, 1980 [DE] Fed. Rep. of Germany ....... 3045332

[51] Int. Cl.³ .................... B01J 31/40; C07C 69/82
[52] U.S. Cl. .................................. 502/24; 502/28; 560/77; 560/78
[58] Field of Search .............. 252/413, 420, 414, 412; 560/77, 78; 423/49; 502/24, 28

[56] References Cited

U.S. PATENT DOCUMENTS

| | | | |
|---|---|---|---|
| 3,914,287 | 10/1975 | Takeda et al. | 560/77 |
| 4,092,481 | 5/1978 | Bunger et al. | 560/77 |
| 4,096,340 | 6/1978 | Fujii et al. | 560/77 |
| 4,126,755 | 11/1978 | Bunger et al. | 560/77 |
| 4,353,810 | 10/1982 | Wendle, Jr. | 252/412 |
| 4,372,875 | 2/1983 | Bunger et al. | 252/413 |

FOREIGN PATENT DOCUMENTS

2923681 10/1980 Fed. Rep. of Germany ...... 252/413

OTHER PUBLICATIONS

Chemical Engineers' Handbook, J. H. Perry, McGraw-Hill Book Co. Inc., N.Y., 1950, Third Edition, pp. 716-718.

Primary Examiner—P. E. Konopka
Attorney, Agent, or Firm—Antonelli, Terry & Wands

[57] ABSTRACT

A process for the recovery and reuse of heavy metal oxidation catalyst from residues in the Witten DMT process by extraction, which involves mixing and settling of the residue with water or dilute aqueous solutions of water-soluble, low-molecular, aliphatic monocarboxylic acids at 70°–160° C. and recycling of the extract of the high-boiling distillation residues into the DMT process. The high-boiling distillation residue and the extractant are used in a quantitative ratio of 1:0.9 to 1:0.1, preferably 1:0.5 to 1:0.3.

15 Claims, 1 Drawing Figure

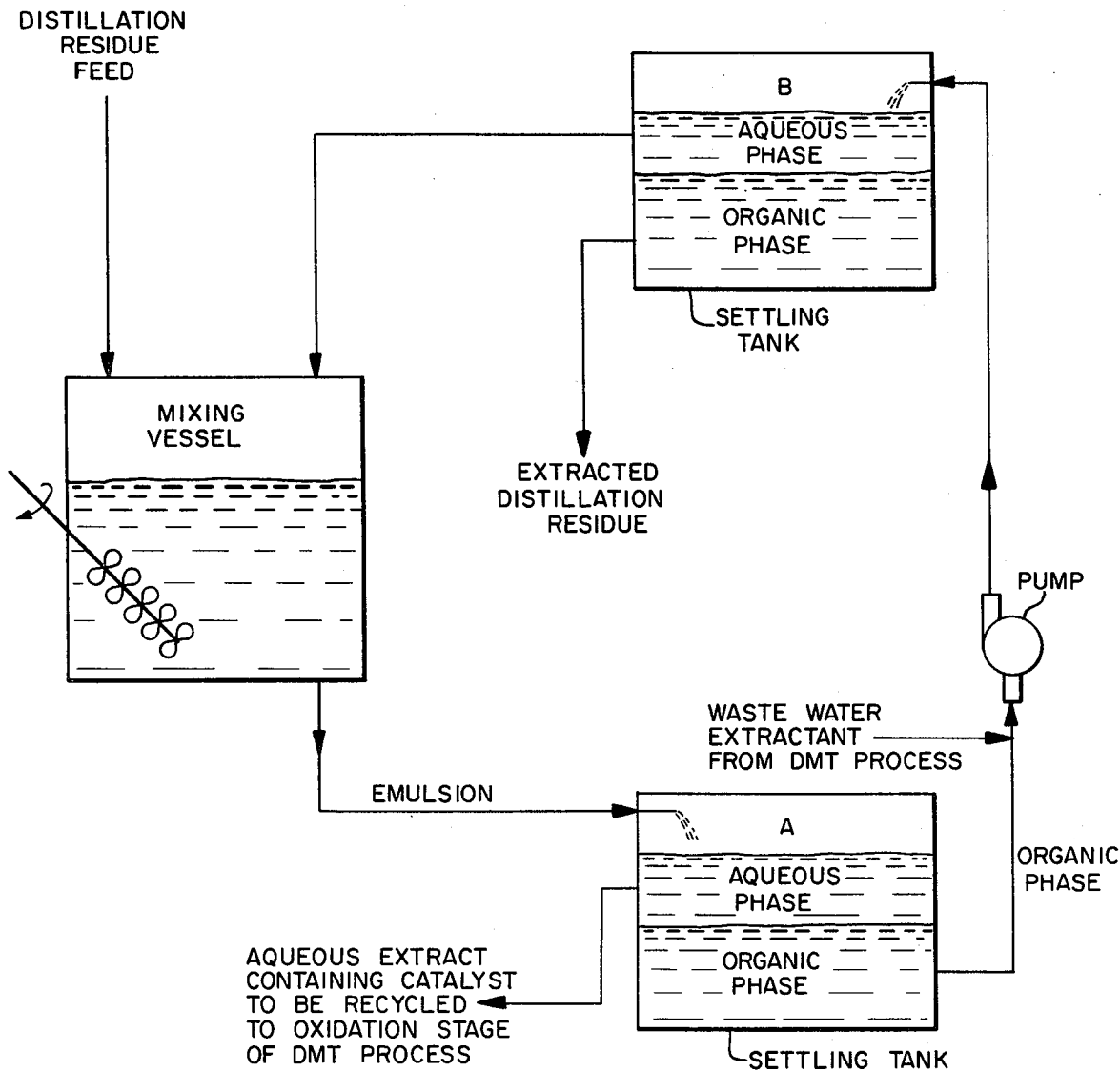

PROCESS FOR THE RECOVERY AND REUSE OF HEAVY METAL OXIDATION CATALYST FROM RESIDUES IN THE WITTEN DMT PROCESS

This application is a continuation in part of application Ser. No. 326,280 filed Dec. 01, 1981 now U.S. Pat. No. 3,372,875 which is continuation of Ser. No. 156,605 filed June 05, 1980 and now abandoned.

The invention relates to a process for the recovery and reuse of heavy metal oxidation catalyst from residues in the Witten DMT process.

Dimethyl terephthalate (DMT) is produced in numerous large-scale technical plants according to the Witten DMT process (as described for example in German Pat. No. 1,041,945). Polyesters are obtained by reacting polyhydric alcohols with DMT. Such high-molecular compounds—also called saturated polyesters—are processed, inter alia, to fibers, filaments, films or molded articles.

According to the Witten DMT process, a mixture of p-xylene (PX) and methyl p-toluate (PTE) is oxidized in the liquid phase in the absence of solvents and halogen compounds under a pressure of about 4–8 bar and at a temperature of about 140°–170° C. with atmospheric oxygen in the presence of dissolved heavy metal catalysts, for example in the presence of a mixture of cobalt and manganese compounds (see German Pat. No. 2,010,137); in addition, still other catalysts have been investigated for the Witten DMT process, containing besides cobalt and/or manganese also nickel, cerium, or beryllium (cf. H. Bunger: "Compendium" 78/79, supplemental issue of periodical "Erdol und Kohle, Erdgas, Petrochemie" [Petroleum and Coal, Natural Gas, Petrochemistry], pp. 417–436).

Following the oxidation stage, the thus-obtained reaction mixture consisting primarily of monomethyl terephthalate (MMT) and of p-toluic acid (PTA) is esterified with methanol under a pressure of about 20–25 bar and at a temperature of about 250°–280° C. The esterification product is separated by distillation into a PTE fraction, a DMT fraction, and a high-boiling, tarry residue. The PTE fraction is recycled into the oxidation. The high-boiling, tarry distillation residue contains, inter alia, all of the metal components of the catalyst system.

There is an industrial need for recovering the oxidation catalysts from the tarry distillation residue and reuse same for the oxidation of PX and PTE.

It has been suggested to recover the oxidation catalyst from high-boiling distillation residue obtained in the DMT production according to the Witten DMT method by a liquid-liquid extraction and to recycle the catalyst-containing extract into the oxidation stage. Extractants proposed in this connection were, for example, water or mixtures of water and water-soluble carboxylic acids (cf. Japanese Patent Application No. 67/42997). Such a liquid-liquid extraction, however, yields extracts having a non-uniform and frequently inadequately low catalytic activity and selectivity; for this reason, various additional measures have been proposed to avoid losses in activity and selectivity (cf. DOS [German Unexamined Laid-Open Application] No. 2,525,135; DAS [German Published Application] No. 2,531,106).

These processes are still not fully satisfactory. Due to incomplete extraction, catalyst losses are incurred, and disturbances in operation are encountered due to emulsion formation. Besides, the catalyst concentrations in the extracts are low, so that the extracts must be concentrated before being reused in the oxidation stage. For raising the concentration, specific devices must be employed, causing considerable initial investment and operating costs. During storage, various compounds are separated from the concentrated extracts due to crystallization; this complicates the handling of the extracts.

Furthermore, the extracts contain trimellitic acid and trimellitic acid monomethyl ester; these compounds can impair the catalytic activity and selectivity (cf. DAS No. 2,923,681).

In the aforementioned processes, iron is also extracted from the distillation residue besides the catalyst components; this iron stems from the material of the apparatus. The iron, with continuous recycling of the extract into the oxidation, is increasingly enriched in the catalyst cycle with increasingly exhaustive extraction of the heavy metals. However, an extensive iron enrichment is undesirable, because this, too, impairs the selectivity of the oxidation. Furthermore, the residue extracted according to the aforementioned processes contains water in all cases, which can be a disturbing factor in any subsequent further use of the residue.

The objectives of the process of this invention thus evolve from the aforedescribed state of the art and the invention seeks to provide the following advantages and effects: the degree of recovery of heavy metal oxidation catalyst is increased; the amount of extractant is reduced; an extract having an increased catalyst concentration and a reduced content of trimellitic acid, trimellitic acid monomethyl ester, and those compounds that crystallize out during storage from the extract; improper iron enrichment in the catalyst circulation is avoided in spite of increased extent of heavy metal extraction; and an extracted residue with a low water content is recovered.

These objectives have been accomplished according to this invention in a process which is characterized by an extraction wherein the extractant and the residue containing the heavy metal catalyst are conducted countercurrently through the extraction stages in a quantitative ratio of residue to extractant of from 1:0.9 to 1:0.1.

The extraction procedure according to the invention wherein the residue and the extractant are conducted countercurrently to each other can consist of two or more extraction stages. With an increasing number of extraction stages, the amount of extractant based on the quantity of residue can be reduced. Two to six extraction stages are advantageous.

According to the state of the art, the distillation residue and the extractant are intermixed for a time of 10–240 minutes. According to the invention, an intermixing of residue with extractant, sufficient for the extraction operation can be achieved even within 0.1–400 seconds, preferably within 0.1–10 seconds. In an especially preferred embodiment of the invention, the feed residue and the extractant are mixed together for a time period of 10–240 minutes in the first extraction stage, and are intermixed in all subsequent extraction stages for a period from 0.1 to 10 seconds. This short-term intermixing can be conducted, for example, by feeding a residue-containing stream and extractant simultaneously into the intake side of a centrifugal pump and pumping them together into the settling tank.

Below the initial boiling point of the aqueous phase (appropriately 100° C.), the degree of extraction becomes higher with an increasing settling temperature; at the same time, the water content of the extracted residue becomes lower. It is thus advantageous to set the temperatures in the settling tanks to be no lower than 70° C.; preferably the settling temperatures are adjusted to be no lower than 15° C. below the initial boiling point of the aqueous phase, and it is particularly advantageous to set the settling temperatures to be no lower than 5° C. below the initial boiling point of the aqueous phase. If the aqueous phase in the settling tanks reach the boiling point, the pressure can rise undesirably, and the phase separation can be slowed down; for this reason, it is advantageous to set the settling temperatures so that no more than 40% by weight of the aqueous phase is removed by evaporation in the settling tanks; it is preferable to adjust the settling temperatures to be not above the initial boiling point of the aqueous phase, and it is especially advantageous to set the settling temperatures to be no higher than 1° C. below the initial boiling point of the aqueous phase.

However, it is possible to use also higher or lower temperatures, if the altered conditions are taken into account, for example, by larger settling tanks, an increased number of extraction stages, and an increased quantity of extractant. The temperatures in the mixers are suitably maintained at the same values as in the settlers.

Under elevated pressure, the boiling curve of the aqueous phase is shifted toward higher temperatures; for this reason, smaller settling tanks can be used at elevated pressure and elevated temperature; the settling temperature, however, is not to be above 160° C. even under elevated pressure. The preferred mode of operation, though, is to conduct the phase separation under normal pressure.

With a decreasing quantitative ratio of aqueous to organic phase, the catalyst concentration in the aqueous extract rises, resulting in advantages because smaller amounts of extract need to be handled and because, with sufficiently high catalyst concentrations, the otherwise required evaporation or some other concentrating step for the extract can be eliminated. However, with a drop in the quantitative ratio of aqueous to organic phase, the degree of extraction is generally diminished.

A special advantage residing in the mode of operation according to this invention is that lower quantitative ratios of aqueous to organic phase can be utilized without a considerable reduction in the degree of extraction. For this reason, the practice in the mode of operation according to the invention is generally to set a quantitative ratio of aqueous to organic phase which is no higher than 9:10, preferably a quantitative ratio of 8:10 or therebelow, especially 5:10. With a very low quantitative ratio of aqueous to organic phase, it may, however, be necessary to increase the number of extraction stages. For this reason, a quantitative ratio of 1:10 will generally form the lower limit; a quantitative ratio of no lower than 2:10 is to be preferred, and especially preferred is a quantitative ratio of 3:10 or more. However, it is, of course, also possible to set quantitative ratios higher than 9:10; although this means that the extract is more greatly diluted, the other advantages attainable by the invention remain intact.

The suitable residence time for the organic phase in the settling tanks depends on the catalyst content of the residue, the number of extraction stages, the settling temperature, and the quantitative ratio of aqueous to organic phase. With too short a residence time, the phase separation is inadequate; too long a residence time leads to an increased volume requirement for the settling tanks. The residence time can be lower in the second and each subsequent settling tank than in the respectively preceding settling tank. The residence time leading to a sufficient phase separation under the respective conditions can be determined by a few experiments.

The DMT content of the distillation residue to be extracted can amount to more than 10% by weight of DMT; it can also be lower, for example, due to an aftertreatment, for example, according to German Pat. No. 2,310,824 or German Pat. No. 2,427,875. If the extraction of this invention is preceded by aftertreatments which substantially increase the viscosity of the residue, then measures must be taken to obtain a sufficient dispersing speed of the aqueous and organic phases in the mixers. A sufficient dispersion rate can be obtained, for example, by setting suitable temperatures in the mixers, or by dilution of the organic phase with a diluent of lower viscosity which is miscible with the residue and shows little or not miscibility with water, for example with p-xylene, mixed xylene, or aromatic esters. In this connection, diluents are to be preferred wherein the density at the extraction temperatures is higher than the density of water, and benzoic acid methyl ester is especially advantageous.

It will be understood that a diluent may be added to the organic phase prior to extraction and if employed, the diluents are mixed preferably at a weight ratio of 1:1 with the residue. A suitable range of viscosity for the organic phase in a mixing unit at the respective operating temperatures is below 300 cp, preferably below 150 cp, and especially below 60 cp.

It is, of course, also possible first to effect the catalyst recovery according to this invention and subsequently a residue aftertreatment.

Suitable extractants for the process of this invention are those already suggested for the extraction of oxidation catalyst from high-boiling distillation residue obtained in the DMT production according to the Witten procedure; aqueous solutions of lower aliphatic carboxylic acids containing 1 to 8 carbon atoms are to be preferred, and the reaction wastewater containing acetic acid and formic acid, as obtained in the oxidation of PX and PTE is especially preferred. This reaction wastewater is produced as a vapor condensate; it can be used as extractant without any further treatment, but its use as extractant can also be preceded by a separation of those components which have a lower boiling point than water.

The extract obtained according to the invention can advantageously be reused directly in the oxidation stage of the Witten DMT process without being evaporated or increased in concentration in some other way, and without having to separate therefrom insoluble cobalt compounds or organic substances.

If an undesirable iron enrichment is determined to exist in the extract obtained according to the invention, the iron content can be reduced to a tolerable value by filtration of the extract; in this connection, it is advantageous to filter the extract at an elevated temperature of from 40° to 95° C. through a coarse-grain auxiliary filtering agent; activated carbon is especially advantageous.

The benefits attainable with the invention reside especially in that a substantially higher catalyst recovery rate is obtained in spite of a considerably reduced quantity of extractant; that an extract is produced having a higher catalyst concentration; that this extract can be utilized in the oxidation stage of the Witten DMT process without being evaporated or raised in concentration in some other way; that the extract does not contain any interfering amounts of compounds separated by crystallization during storage; that the content of trimellitic acid and trimellitic acid monomethyl ester in the extract, based on its content of oxidation catalyst, is diminished; that the extracted residue contains a smaller quantity of water; and that, in spite of an increased degree of catalyst recovery, there is no improper iron enrichment in the catalyst cycle.

The apparatus for carrying out the process of this invention is illustrated in the accompanying sole FIGURE which is a schematic flow sheet.

The following Examples 1 and 2 illustrate the mode of operation according to this invention and the advantages realizable by this invention, and Comparative Examples 3 and 4 illustrate the state of the art on which the invention is based.

EXAMPLE 1

The entire distillation residue was extracted, as obtained in the raw ester distillation of an industrial plant for DMT manufacture according to the Witten process in an apparatus as shown in the accompanying sole FIGURE.

In this plant, PX and PTE were jointly subjected to continuous oxidation in the liquid phase at an excess pressure of 5-7 bar and at a reaction temperature of 150°-170° C. in a cascade of three oxidation reactors; the oxidation catalyst employed was a solution of cobalt acetate and manganese acetate in the water of reaction produced as waste material in this oxidation and obtained as a vapor condensate; this reaction wastewater contains, on the average, 2.5% by weight of acetic acid, 1.5% by weight of formic acid, 6.0% by weight of methanol, and 0.8% by weight of formaldehyde. This fresh catalyst solution was fed continuously into the first oxidation reactor of the cascade, so that a stationary concentration was obtained in the oxidation product of 90 ppm cobalt and 9 ppm manganese. The oxidation product contained, besides the aforementioned catalyst and the thus-produced carboxylic acids, unreacted feed and various intermediate products and by-products. This oxidation product was continuously esterified with methanol at temperatures of about 250° C. and under pressures of between 20 and 30 bar. The esterification product was continuously separated by vacuum distillation; the components boiling higher than DMT were subjected to a thermal aftertreatment under vacuum, thus obtaining additional DMT from the high-boiling components by distillation.

The resultant distillation residue contained 0.40% by weight of cobalt and 400 ppm manganese. This residue was fed continuously (2t/h) to a mixing vessel equipped with an agitator. In this mixing vessel, the residue was mixed with the aqueous phase (0.53t/h) discharged from a container designated "settling tank B." An emulsion (2.53t/h) was continuously withdrawn from the mixing vessel through a bottom valve and fed into a container designated "settling tank A" where it was separated into an aqueous phase and a residue-containing organic phase. Both phases were discharged continuously from the settling tank A. The organic phase (2 t/h) was pumped by a centrifugal pump from settling tank A into the settling tank B; the intake pipe of this centrifugal pump was charged, simultaneously with the organic phase, also with the above-described reaction wastewater (0.53t/h), which contains acetic acid and formic acid; both components were jointly pumped into settling tank B. One part by weight of extractant was utilized per 3.75 parts by weight of residue. The temperatures in the mixing vessel and in the settling tanks were maintained at 94° C. The average residence time in the mixing vessel was 4 hours; the average residence time in the centrifugal pump was 1.2 seconds; the average residence time of the continuous organic phase in settling tank A was 20 hours; the average residence time of the continuous organic phase in settling tank B was 10 hours. (The term "continuous organic phase" means that in the settler only the continuous organic phase formed after phase separation is used to calculate the residence time.)

Extracted residue (2t/h) was discharged from settling tank B, containing 8 ppm cobalt and less than 1 ppm manganese, representing a recovery rate of 99.8%. This residue is removed from the system.

The water content of this extracted residue, determined according to the Karl Fischer method, was 0.35% by weight.

The aqueous phase discharged from the settling tank A (0.53t/h) contained 1.5% by weight of cobalt, 0.15% by weight of manganese, in total 0.74% by weight of trimellitic acid and trimellitic acid monomethyl ester, as well as 230 ppm iron. This solution was stored for 240 hours at 80° C., obtaining 1.2 g of solid matter due to crystallization per liter of solution. The quantitative ratio of aqueous phase to organic phase in this example is 2.7:10.

EXAMPLE 2

The mode of operation of Example 1 was followed using the same flow rates of extractant, residue, etc. with the sole exception that the solution discharged from settling tank A was filtered through a coarse-grained activated carbon. The results obtained were essentially the same as in Example 1, the only difference being that the iron content of the thus-filtered solution was 15 ppm. This solution was recycled into the first oxidation reactor of the oxidation cascade described in Example 1; oxidation was accomplished with this catalyst solution without any difficulties. No additional fresh catalyst was added any longer to the oxidation stage and the oxidation could be continued without disturbances and with yields comparable to those obtained with fresh catalyst. In this example, the catalyst solution contains 1.5% by weight of cobalt, 0.15% by weight of manganese, a total of 0.74% by weight of trimellitic acid and trimellitic acid monomethyl ester and 15 ppm iron after 240 hours of storage at 80° C., 1.2 g of solid compounds were crystallized per liter of solution.

EXAMPLE 3

(Comparative Example)

The residue described in Example 1 at a rate of 2t/h was mixed with 2t/h of the extractant of Example 1 in the mixing vessel described in Example 1; the resultant emulsion (4t/h) was discharged through the bottom valve into the settling tank A and separated therein into an aqueuous phase and a residue-containing organic phase. One part by weight of extractant was used per part by weight of residue. The temperatures in the mixing vessel and in the settling tank were maintained at 94° C. The average residence time in the mixing vessel was 2.7 hours, the average residence time of the continuous organic phase in the setting tank was 30 hours.

Extracted residue (2t/h) was withdrawn from the settling tank, containing 320 ppm cobalt and 32 ppm manganese; this constitutes a recovery rate of 92%.

The water content of the extracted residue was 3.2% by weight.

The aqueous phase discharged from the settling tank contained 0.37% by weight of cobalt and 370 ppm manganese. This aqueous phase (2t/h) was evaporated and, after evaporation, contained 1.5% by weight of cobalt, 0.15% by weight of manganese, in total 1.6% by weight of trimellitic acid and trimellitic acid monomethyl ester, as well as 270 ppm iron. The evaporated solution was stored for 240 hours at 80° C.; during storage, 32 g of solid matter was crystallized per liter of evaporated solution, which solid matter had to be separated prior to using the solution in the oxidation stage. The quantitative ratio of aqueous phase to organic phase in this example is 10:10.

EXAMPLE 4

(Comparative Example)

The residue (2t/h) described in Example 1 was extracted with the extracted (1t/h) of Example 1 under the same conditions as set forth in Example 3, except for the sole difference that one part by weight of extractant was used per two parts by weight of residue. In this case, a recovery rate of merely 67.6% was the result, and the water content of the extracted residue was 4.1% by weight. The aqueous phase discharged from the settling tank contained 0.50% by weight of cobalt and 0.05% by weight of manganese. After evaporation, the aqueous phase contained 1.5% by weight of cobalt, 0.15% by weight of manganese, in total 1.5% by weight of trimellitic acid and trimellitic acid monomethyl ester, as well as 220 ppm iron. The evaporated solution was stored for 240 hours at 80° C., thus crystallizing 26 g of solid matter per liter of evaporated solution, which had to be separated prior to using the solution in the oxidation stage.

What is claimed is:

1. An extraction process for the recovery and reuse of heavy metal oxidation catalyst from the high-boiling distillation residue in the Witten process for producing dimethyl terephthalate, said high-boiling distillation residue being obtained in the oxidation of mixtures containing p-xylene and methyl p-toluene in the liquid phase with oxygen or an oxygen-containing gas under elevated pressure and at elevated temperature in the presence of dissolved heavy metal oxidation catalyst, subsequent esterification of the oxidation product with methanol under elevated pressure and at elevated temperature and distillatory separation of the esterification product into a raw dimethyl terephthalate fraction, a fraction rich in methyl p-toluate, and a high-boiling distillation residue containing the oxidation catalyst, which comprises mixing an organic phase, resulting from an aqueous pre-treatment of the high-boiling distillation residue, with an extractant comprising water or a diluent aqueous solution of at least two water soluble, low-molecular weight, aliphatic monocarboxylic acid at 70° to 160° C.; introducing the resulting mixture of extractant and organic phase into a first settling tank, discharging a first aqueous phase from said settling tank, introducing said first aqueous phase into a mixing vessel, introducing the distillation residue into said mixing vessel, discharging an emulsion of the first aqueous phase and said distillation residue from said vessel into a second settling tank, discharging an aqueous extract from said second settling tank containing a major portion of the catalyst initially present in said distillation residue and withdrawing the organic phase to be mixed with said extractant from said second settling tank; the high-boiling distillation residue and the extractant being employed in a quantitative weight ratio of one part of residue per 0.9 to 0.1 part of the extractant and the organic phase initially separated from the emulsion and the extractant being mixed together at temperatures between 85° and 100° C. within a period of from 0.1 to 400 seconds.

2. The process according to claim 1, characterized in that the catalyst-containing extract is filtered to remove iron impurities before being recycled into the oxidation.

3. The process according to claim 1, characterized in that the organic phase prior to extraction is combined with a diluent of a lower viscosity, said diluent being miscible with the residue and being poorly miscible or immiscible with water.

4. The process according to claim 3, characterized in that the methyl ester of benzoic acid is utilized as the diluent of lower viscosity.

5. The process according to claim 1, wherein the distillation residue and the first aqueous phase are mixed together for a period of from 10 to 240 minutes in said mixing vessel.

6. The process according to claim 1, characterized in that the high-boiling distillation residue and the extractant are conducted counter-currently in a quantitative weight ratio of one part of residue per 0.5 to 0.3 part of the extractant.

7. The process according to claim 1, wherein the extractant is a reaction waste water that is obtained from the oxidation of p-xylene and methyl p-toluate and that contains acetic acid and formic acid.

8. The process according to claim 1, wherein the extractant and the organic phase initially separated from the emulsion are mixed in a centrifugal pump and the resulting admixture is pumped into said first settling tank.

9. The process according to claim 1, wherein said aqueous pre-treatment includes admixing the high-boiling distillation residue with water in the mixing vessel to form an emulsion, thereafter, effecting separation of the emulsion into an aqueous phase and into said organic phase to be mixed with said extractant.

10. The process according to claim 1, further comprising discharging an organic phase from said first settling tank which contains extracted distillation residue.

11. The process according to claim 1, wherein the temperatures of the settling tanks are set to be no lower than 70° C. below the initial boiling point of the aqueous phase contained therein.

12. The process according to claim 5, wherein the extractant is a reaction waste water that is obtained from the oxidation of p-xylene and methyl p-toluate and that contains acetic acid and formic acid.

13. The process according to claim 5, wherein the extractant and the organic phase initially separated from the emulsion are mixed in a centrifugal pump and the resulting admixture is pumped into said first settling tank.

14. The process according to claim 5, wherein said aqueous pre-treatment includes admixing the high-boiling distillate residue with water in the mixing vessel to form an emulsion, thereafter effecting separation of the emulsion into an aqueous phase and into said organic phase to be mixed with said extractant.

15. The process according to claim 5, further comprising discharging an organic phase from said first settling tank which contains extracted distillation residue.

* * * * *